(12) United States Patent
Marks et al.

(10) Patent No.: US 7,485,094 B2
(45) Date of Patent: Feb. 3, 2009

(54) METHODS OF DIAGNOSIS USING PULSE VOLUME MEASUREMENT

(75) Inventors: Lloyd Marks, Westfield, NJ (US); Michael Smith, Oradell, NJ (US)

(73) Assignee: Smithmarks, Inc., Ridgefield, NJ (US)

( * ) Notice: Subject to any disclaimer, the term of this patent is extended or adjusted under 35 U.S.C. 154(b) by 462 days.

(21) Appl. No.: 10/673,167

(22) Filed: Sep. 30, 2003

(65) Prior Publication Data

US 2005/0070807 A1 Mar. 31, 2005

(51) Int. Cl.
*A61B 5/02* (2006.01)
(52) U.S. Cl. .................. 600/504; 600/500; 600/507
(58) Field of Classification Search .......... 600/500–507
See application file for complete search history.

(56) References Cited

U.S. PATENT DOCUMENTS

| | | | | |
|---|---|---|---|---|
| 3,796,213 | A * | 3/1974 | Stephens | 600/479 |
| 4,548,211 | A * | 10/1985 | Marks | 600/507 |
| 5,241,963 | A * | 9/1993 | Shankar | 600/481 |
| 5,715,828 | A * | 2/1998 | Raines et al. | 600/507 |
| 5,718,232 | A * | 2/1998 | Raines et al. | 600/507 |
| 6,149,587 | A * | 11/2000 | Raines | 600/300 |
| 2004/0043614 | A1 * | 3/2004 | Koizumi | 438/689 |
| 2005/0107712 | A1 * | 5/2005 | Arnold | 600/500 |

OTHER PUBLICATIONS

AHA Scientific Statement: Diagnosis and Treatment Chronic Arterial Insufficiency of the Lower Extremities: A Critical Review (Weitz et al.) Circulation: 94(11), 1996; 3206-3049.*

* cited by examiner

*Primary Examiner*—Robert L Nasser
*Assistant Examiner*—Karen E Toth
(74) *Attorney, Agent, or Firm*—Blank Rome LLP (57) ABSTRACT

The utility of pulse volume measurement is expanded to detection of many conditions which have previously not been detected or have been detected using more complicated techniques. Such conditions include blood loss, septic shock, cardiogenic shock, neonatal sepsis, patent ductus arteriosus, limb ischemia, intra-aortic balloon pump performance, peripheral vascular disease, congestive heart failure, the effectiveness of vasoactive medications, syncope, dehydration, pre-eclampsia, deep vein thrombosis, thermal injuries, vascular instability due to renal dialysis, compromising of circulation to the hand caused by radial artery harvesting, changes in cardiac output, and hypertension. According to the present invention, such diagnoses can be performed by taking one measurement, by taking measurements over time to detect a change or by taking measurements before and after application of a treatment or stimulus.

5 Claims, 8 Drawing Sheets

FIG. 3A
PRE-BALLOON INSERTION

FIG. 3B
POST-BALLOON INSERTION (IN LEFT LEG) BEFORE PUMP STARTED

FIG. 3C
IABP RUNNING
(BALLOON IN LEFT LEG)

FIG. 3D
IABP STANDBY
(BALLOON IN LEFT LEG)

FIG. 3E
IABP BACK ON
(BALLOON IN LEFT LEG)

FIG. 3F

CHANGE IN LOWER LIMB PULSE VOLUME RATIO AFTER BALLOON INSERTION

FIG. 3H

FLOW AUGMENTATION IN LEFT ARM

FIG. 3I

FLOW AUGMENTATION IN RIGHT LEG

FIG. 3G

ARM AND LEG PULSE VOLUME WITH AND WITHOUT IABP

METHODS OF DIAGNOSIS USING PULSE VOLUME MEASUREMENT

FIELD OF THE INVENTION

The present invention is directed to methods of diagnosis using pulse volume measurement and more particularly to diagnostic methods which expand the utility of pulse volume measurement.

DESCRIPTION OF RELATED ART

The measurement of peripheral blood flow is important in medicine, since there are many specific diseases in which peripheral blood flow is impaired, e.g., diabetes and atherosclerosis. Also, the peripheral blood flow is altered as the total cardiac output is increased or decreased. Cardiac output is particularly important in patients who are under anesthesia, are in the post-operative state, or are critically ill or unstable. As blood flow from the heart falls, the peripheral blood flow is dramatically reduced to preserve flow to the brain and vital organs.

Blood flow to an extremity can be measured painstakingly and invasively by dissecting out the main blood vessels to the limb (e.g., brachial artery in an arm) and encircling it with an electromagnetic flow probe. That is clearly not a technique suitable for clinical use. It is therefore desired to measure peripheral blood flow non-invasively.

Peripheral impedance (or conductance) plethysmography is a technique for non-invasively measuring peripheral pulse volume, which is the small change in the volume of a limb segment occurring within the cardiac cycle. Peripheral blood flow or peripheral perfusion are closely related to the pulse volume. The technique works by obtaining a raw pulse volume analog signal and applying a selective signal-averaging algorithm to the raw pulse volume signal. The technique is described in U.S. Pat. No. 4,548,211 to Marks.

Figure 1:
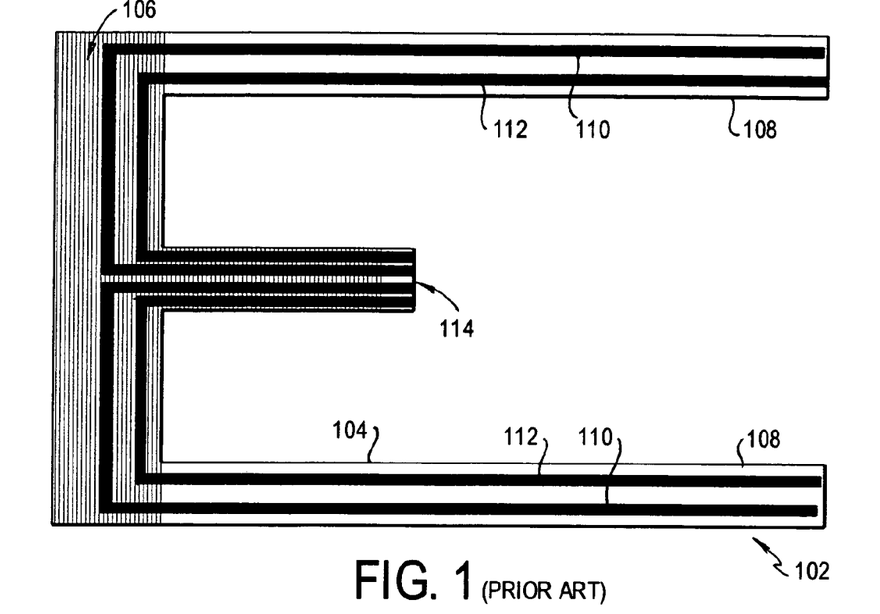
FIG. 1 shows a known electrode configuration for plethysmography.

In the technique as currently practiced, the raw pulse volume analog signal is obtained by measuring the electrical impedance (or conductance) of a limb segment with an electrode such as that of FIG. 1. The electrode 102 is made of a flexible material 104, so that it can be wrapped around the limb segment. The flexible material is configured to define a connecting portion or member 106, which is insulated from direct electrical contact with the patient, and two members 108 for being wrapped around or otherwise applied to the limb segment. Each of the two members 108 contains an outer current electrode 110 paired with an inner voltage electrode 112. An electrical connector 114 allows the outer current electrodes 110 and the inner voltage electrodes 112 to be connected to a source of current and a voltage measuring device, respectively.

An alternating current on the order of 1 ma amplitude and 40 kHz frequency is applied to the two outer current electrodes, while the inner voltage electrodes are used to measure the voltage resulting from the applied current. The ratio of the amplitude of the voltage waveform to the amplitude of the current waveform is the limb impedance, Z. Measurements of Z over time provide the baseline impedance $Z_0$ of the limb segment and the pulsatile change $\Delta Z$ of the impedance. Knowing the resistivity $\rho$ of the blood and the distance L between the two inner voltage electrodes, the change in volume $\Delta V$ can be calculated as:

$$\Delta V = \rho L^2 \Delta Z / Z_0.$$

The resistivity $\rho$ is either calculated or approximated from the patient's hematocrit. The distance L has traditionally been measured with a measuring device, such as a ruler, and then the value of L has been manually input into the device which performs the calculations.

An improvement to the device of the Marks patent is described in U.S. patent application Ser. No. 10/392,308 by Smith et al, filed Mar. 20, 2003, entitled "Peripheral Impedance Plethysmography with Detection of Electrode Spacing." That improvement provides an automatic determination and input of the inter-electrode spacing L. However, no additional uses for peripheral impedance plethysmography are described in that application.

SUMMARY OF THE INVENTION

It will be readily apparent from the above that a need exists in the art to extend the use of plethysmography to diagnose more conditions. To that end, the present invention is directed to varied techniques using plethysmography to detect conditions that have previously not been detected or have been detected using more complicated techniques. Such conditions include blood loss, septic shock, cardiogenic shock, neonatal sepsis, patent ductus arteriosus, limb ischemia, intra-aortic balloon pump performance, peripheral vascular disease, congestive heart failure, the effectiveness of vasoactive medications, syncope, dehydration, pre-eclampsia, deep vein thrombosis, thermal injuries, vascular instability due to renal dialysis, compromising circulation to the hand caused by radial artery harvesting, changes in cardiac output, and hypertension.

Throughout the present disclosure, it will be understood that the first derivative of pulse volume, dV/dt, provides the instantaneous net inflow into the limb segment. The peak value of the instantaneous net inflow will be referred to as the peak net inflow and will be abbreviated PNI. Other parameters that relate to peripheral blood flow are the area under the pulse volume curve (PV–area) and the pulse volume×heart rate product (PV×HR). Recitations of pulse volume measurements or of steps of taking pulse volume measurements should therefore be construed broadly to include any such parameters, unless specifically limited.

BRIEF DESCRIPTION OF THE DRAWINGS

The preferred embodiments of the present invention are disclosed in detail with reference to the drawings, in which.

DETAILED DESCRIPTION OF THE PREFERRED EMBODIMENTS

Preferred embodiments are set forth in detail herein with reference to the drawings. First, three general procedures will be outlined. Then, their application to various uses will be described in detail.

Figure 2A:
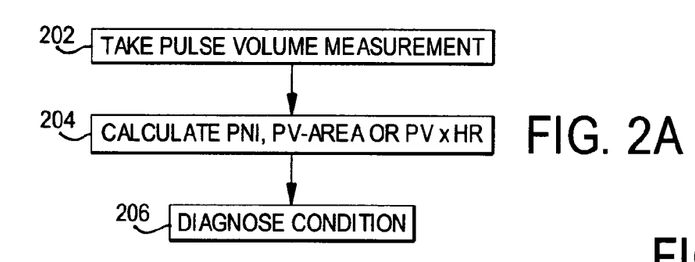
FIGS. 2A-2C show flow charts of the procedures used in the preferred embodiments.

The most general procedure is shown in the flow chart of FIG. 2A. A pulse volume measurement is taken once or more than once in step 202, using a suitable device, such as, for example, any of the devices disclosed in the above-cited Marks patent and Smith et al patent application. Then, if required, the PNI (or PV–area OR PV×HR) is calculated in step 204. The condition is diagnosed in step 206.

Figure 2B:
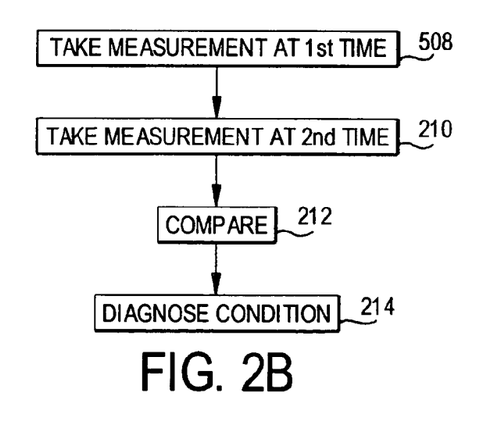

Some conditions, as will be explained below, must be diagnosed in accordance with a change in time of the pulse volume or the PNI (or PV-area or PV×HR). In that case, as shown in FIG. 2B, the measurements are taken at different times in steps 208 and 210 and compared in step 212; then the diagnosis is made in step 214.

Figure 2C:
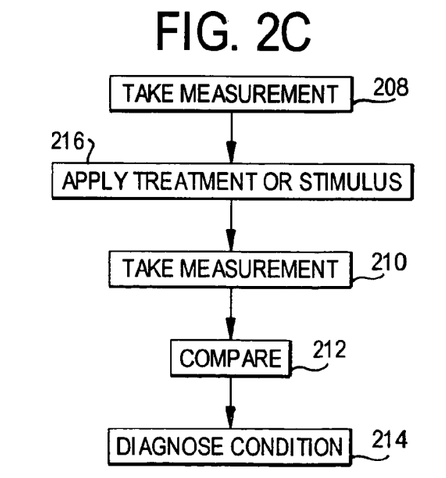

Still other conditions, as well as evaluation of treatment and testing of new treatments, require that measurements be taken before and after treatment or the application of some stimulus to the patient. As shown in FIG. 2C, the measurements are taken in steps 208 and 210 before and after treatment or the application of stimulus in step 216. Then, the comparison of step 212 and the diagnosis or evaluation of step 214 are carried out.

The techniques just described can be performed with a known plethysmography device, such as those disclosed in the above-cited Marks patent and Smith et al patent application. Alternately, the device can be adapted to a particular technique; for example, in the neonatal embodiments to be disclosed below, the electrode is adapted for use on a newborn.

Now, the application of the foregoing broadly disclosed techniques to the various conditions to be diagnosed or evaluated will be described in detail.

1. Detection and treatment of blood loss: The pulse volume monitor has been shown to be sensitive to changes in peripheral vascular flow secondary to blood loss. It is used in the operating room to detect occult blood loss because the quantification of visible blood loss is traditionally difficult. Baseline pulse volume measurements are made prior to starting surgery, and drops in pulse volume are an indication that hypovolemia secondary to hemorrhage may have taken place. Similarly, blood loss is evaluated in the trauma patient. When the trauma patient is first seen by medical personnel, they may have suffered significant internal blood loss. Pulse volume measurements are taken and, based upon normal tables, an initial evaluation is made to determine if significant hypovolemia is present. After initial measurements are made, pulse volume is tracked to see if additional significant blood loss results which would cause a further decrease in pulse volume. Similarly, after surgery, there is often occult blood loss in the post-operative period. Patients are monitored with the pulse volume device to see if there are significant decreases in pulse volume which may indicate that there is occult hemorrhage postoperatively. A rare complication of intra-aortic balloon pumping is rupture of the femoral artery upon removal of a perforated blood-filled balloon. This can result in occult retroperitoneal blood loss which causes a decrease in pulse volume. In addition to detecting blood loss, the pulse volume monitor is used to evaluate the effectiveness of blood transfusion. As the circulating blood volume returns to normal, the pulse volume measurements also return towards normal. These measurements, of course, must be taken in the context that other conditions may be present which could affect pulse volume, such as cardiogenic shock.

2. Septic shock is a condition which is associated with cardiovascular collapse and peripheral vasodilatation. According to the invention, patients at risk for septic shock are monitored with the pulse volume device. Vascular instability can be noted with acute changes in pulse volume accompanying septic shock.

3. Cardiogenic shock: Patients who are in cardiogenic shock have decreased cardiac output and decreased peripheral vascular flow. This results in decreased pulse volume. This is used clinically to detect cardiogenic shock and to evaluate the effective of treatment. With the effective treatment of cardiogenic shock, peripheral vascular flow returns, and pulse volume returns to normal.

4. Neonatal sepsis. Very low birth weight infants are at risk for infection and can develop devastating neonatal sepsis which can lead to cardiovascular instability and death. The pulse volume device is used to monitor these high-risk infants. It is anticipated that large changes in pulse volume, either increasing or decreasing occurs when a patient becomes septic.

5. Patent ductus arteriosus: A patent ductus arteriosus is an abnormal condition in newborn infants in which pulse volume is increased. It is caused by the persistence of a vessel, the "ductus arteriosus," which should close shortly after birth. When a diagnosis of patent ductus arteriosus is made clinically, pulse volume measurements are made to determine the value of pulse volume associated with the presence of a patent ductus in the particular patient. The patient then is monitored; the pulse volume decreases when the ductus arteriosus closes and increases if and when it reopens. Indomethacin is a potent vasoconstrictor that is used to close the ductus arteriosus. It is desirable to use as small a dose as possible because of adverse effects it may have upon the kidney and cerebral circulation. The pulse volume monitor is used to evaluate and monitor the effectiveness of Indomethacin treatment. Sometimes, after a single dose of Indomethacin, the ductus reopens. The pulse volume device provides an indication that the ductus arteriosus has reopened when the pulse volume increases. Additional doses of Indomethacin are given, usually up to a total of three doses, and each time, the effectiveness or lack thereof is evaluated by pulse volume measurement.

6. Limb ischemia monitoring (particularly with intra-aortic balloon pump use): The large catheters that are used for intra-aortic balloon pumping are associated with an approximately 3% incidence of severe limb ischemia. There is currently no satisfactory method for alerting the medical staff that limb ischemia is impending. The pulse volume device is used in the management of this problem. Bilateral lower limb measurements are made prior to insertion of the balloon pump catheter. Thereafter, while the catheter is in position, the ratio of the pulse volume in the catheterized leg to the pulse volume in the other leg is computed. If there is a significant decrease in this ratio, it alerts the medical staff to check for the possibility of limb ischemia. The device incorporates alarms that sound and/or flash if this ratio should decrease below a preset value. The pulse volume device is also used in limb selection for intra-aortic balloon pump catheter insertion. The limb with the greater pulse volume and/or PNI (or PV-area or PV×HR) is a better candidate for balloon pump catheter insertion. Limb ischemia can also occur in a patient who is wearing a cast that is too tight. Pulse volume and/or PNI (or PV-area or PV×HR) measurements are made distal to the cast (if necessary on the fingers or toes) and compared to the contralateral limb. Large discrepancies may indicate that limb perfusion is decreased.

7. Intra-aortic balloon pump performance: Currently the timing of counterpulsation is somewhat of an "art." It is desirable to adjust this timing to maximize cardiac output. Since cardiac output is closely related to peripheral vascular flow, the pulse volume device is used to assist medical personal in adjusting the intra-aortic balloon pump parameters. Intra-aortic balloon pumps provide flow augmentation in diastole. Diastolic flow augmentation may be quantified by lining up the systolic portions of the PV curves measured on and off the pump or at different pump settings. The area between 2 such curves is directly related to the difference in diastolic flow between the two settings. In short, the timing is adjusted to maximize the area between the curves. This effect should be seen in both catheterized and un-catheterized limbs.

Experimental results are shown in FIGS. 3A-3I.

FIGS. 3A-3E show data taken, respectively, before balloon insertion, after balloon insertion but before the pump is started, with the pump running and the balloon in the left leg, during pump standby with the balloon in the left leg, and with the pump back on and the balloon in the left leg. These figures show how the device picks up a decrease in flow to the leg that has the balloon catheter in it.

Figure 3A:
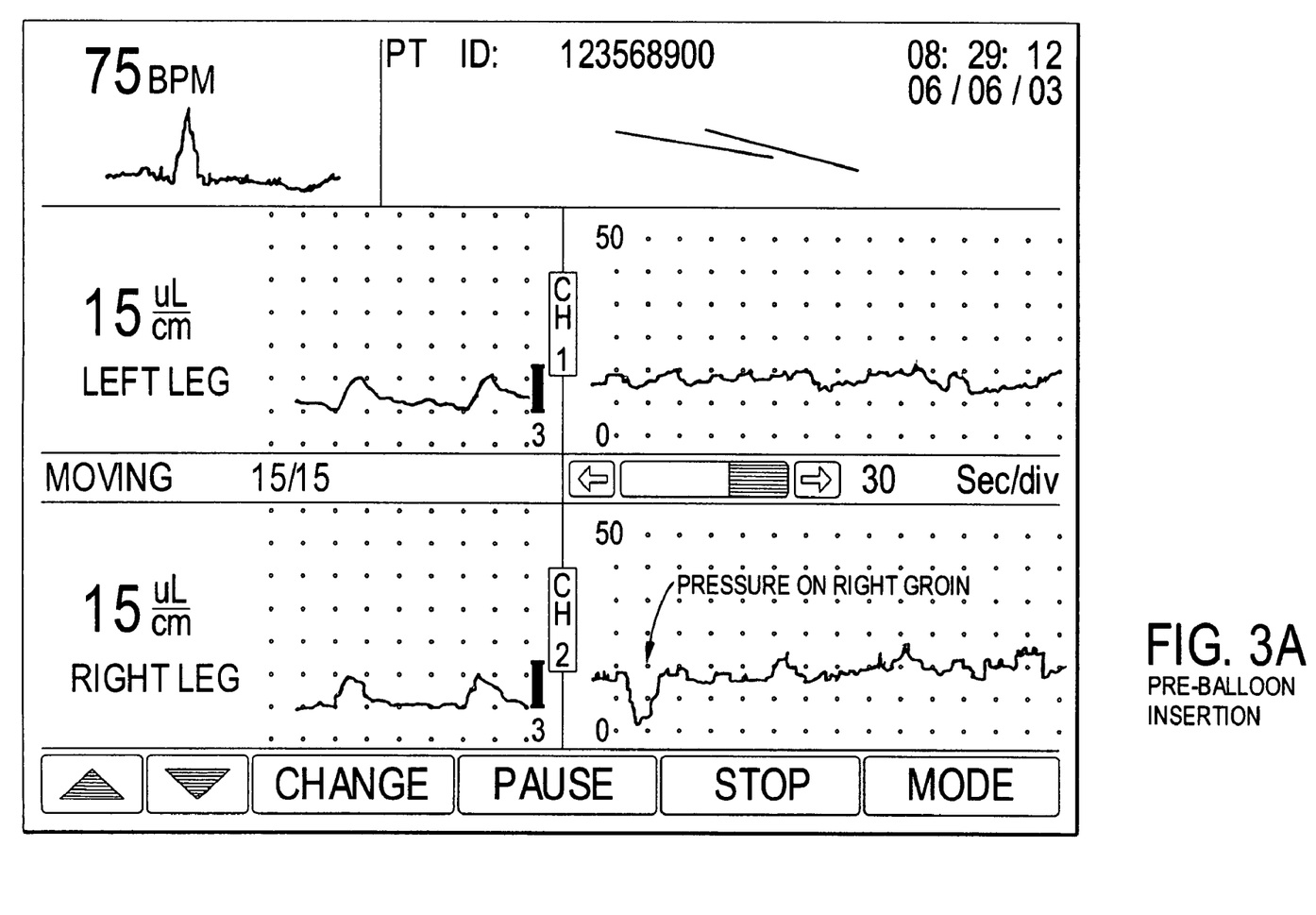
FIGS. 3A-3I show experimental results from one of the preferred embodiments.
Figure 3B:
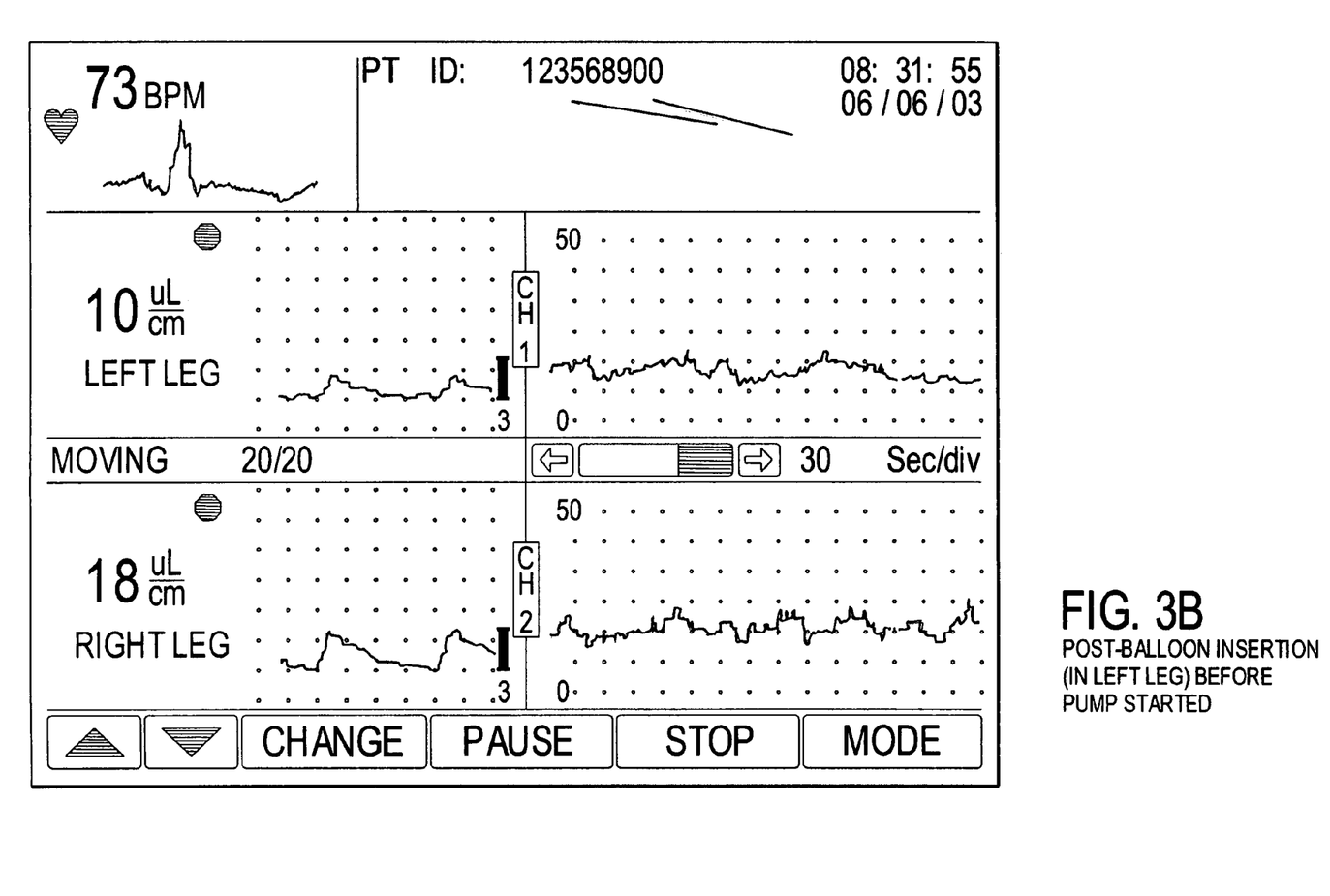
Figure 3C:
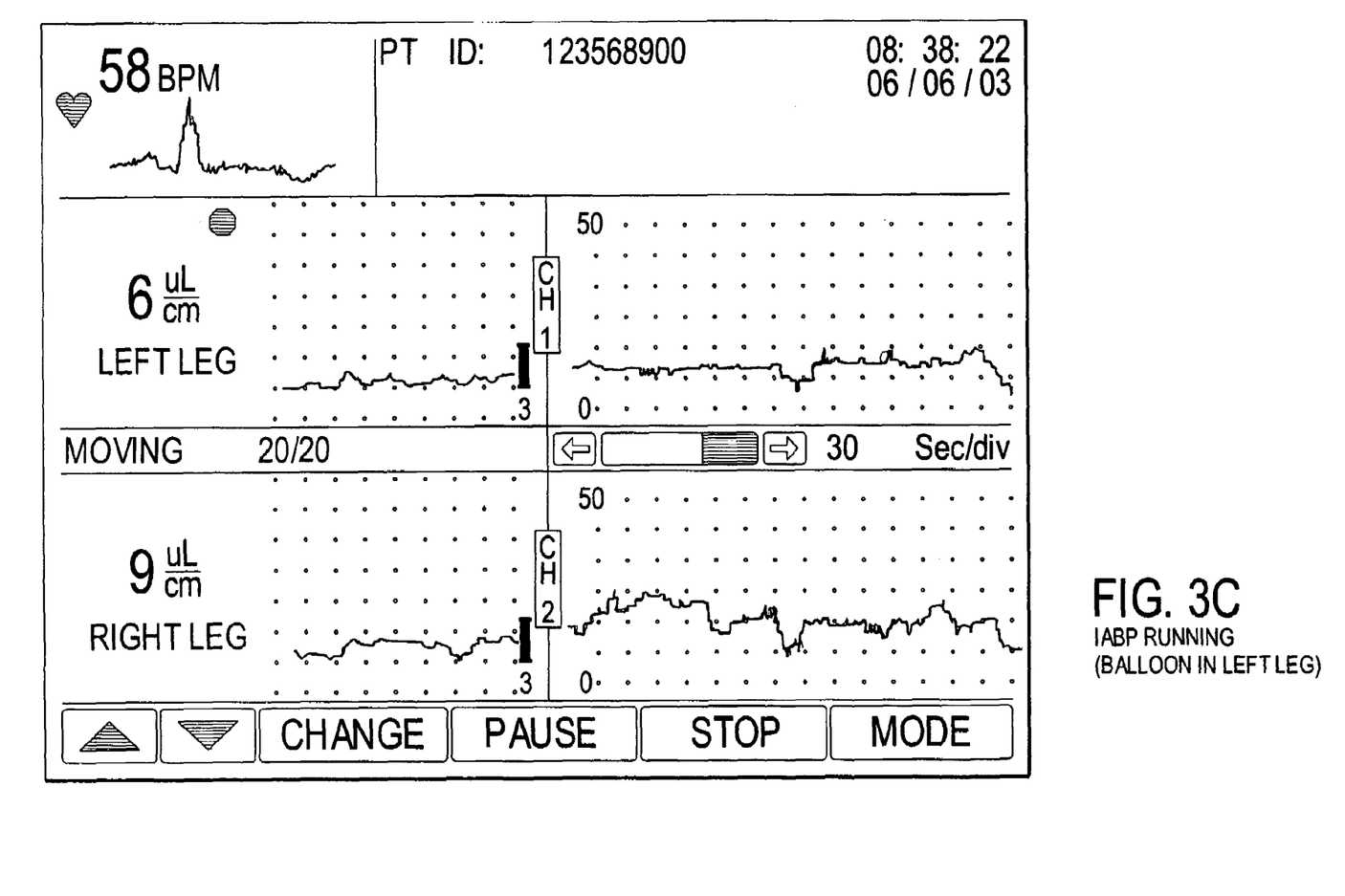
Figure 3D:
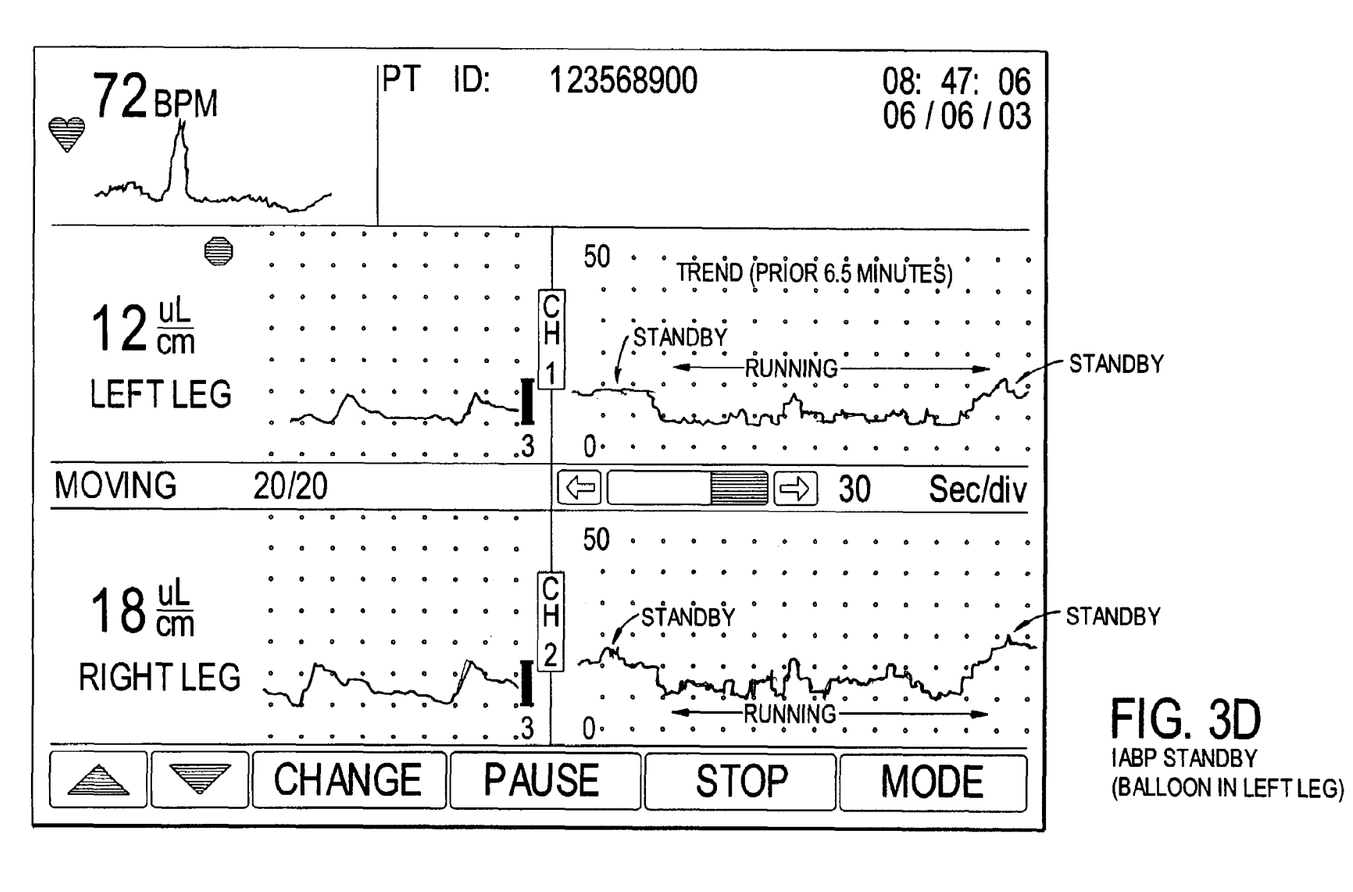
Figure 3E:
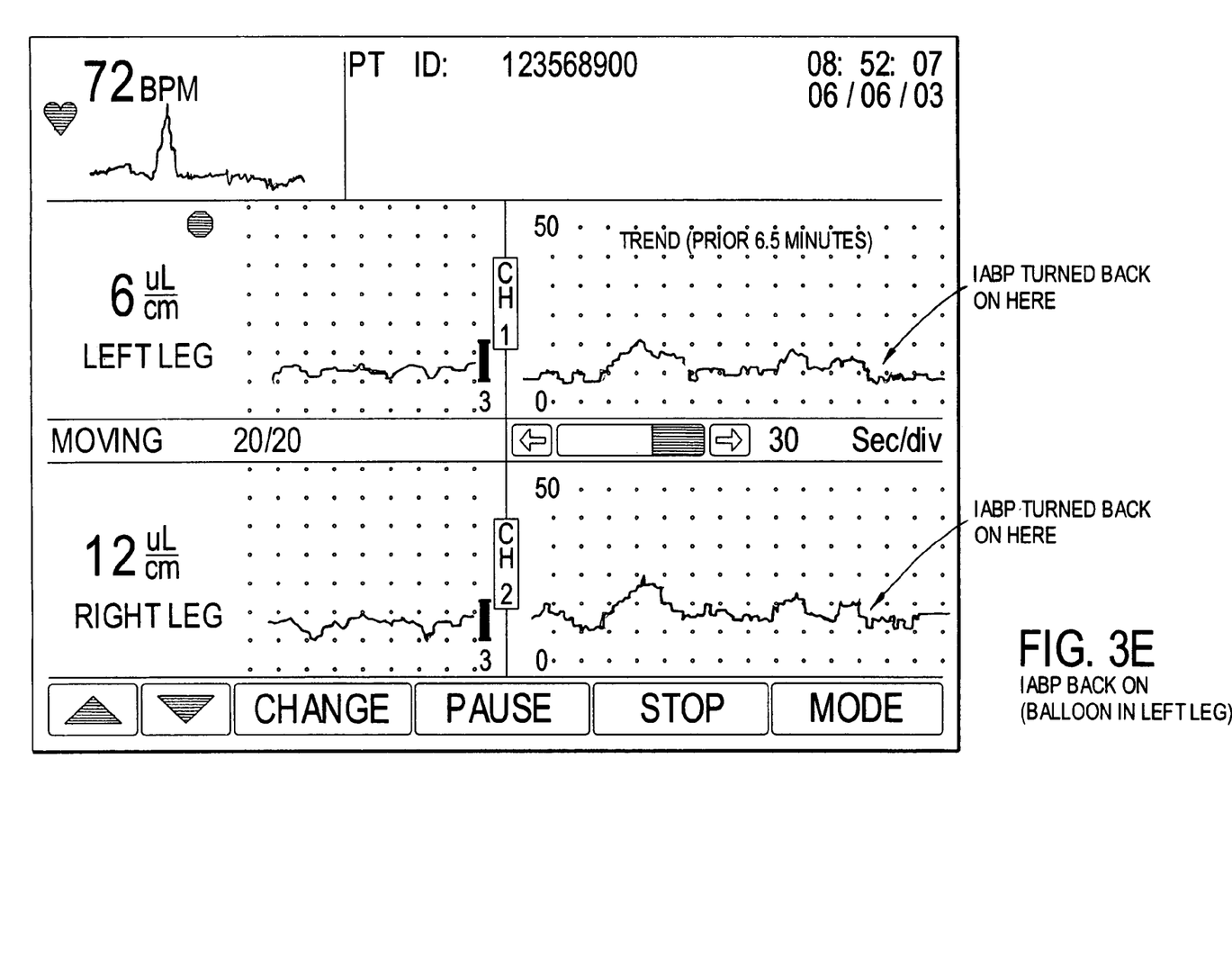
Figure 3F:
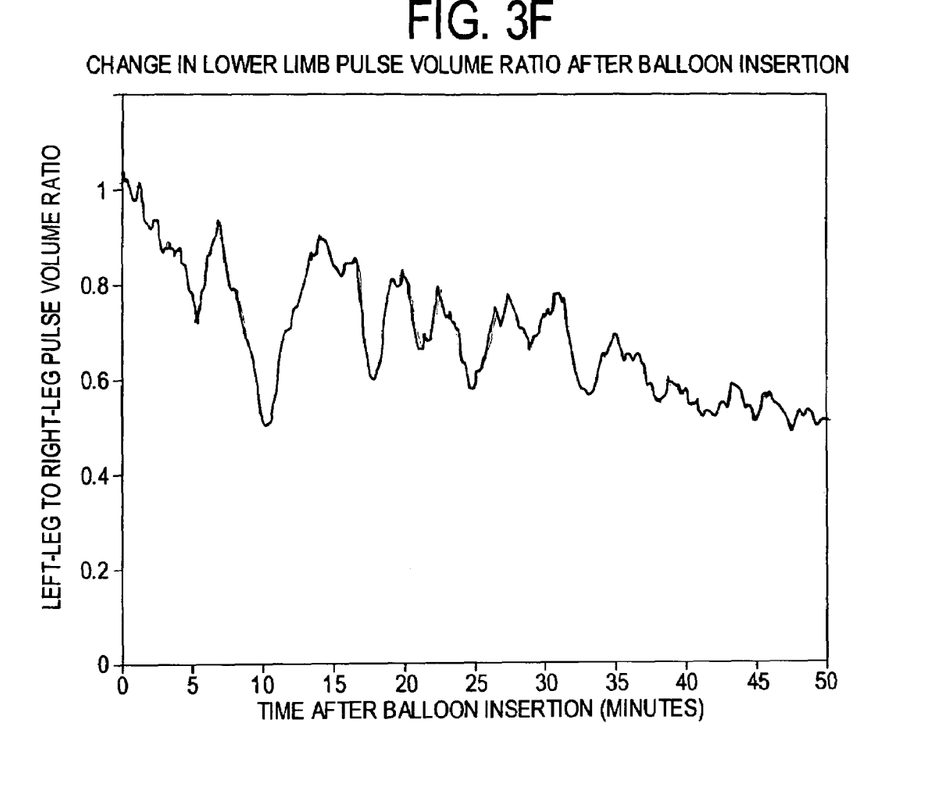

FIG. 3F shows a change in lower limb pulse volume ratio after balloon insertion as a function of time from 0 to 50 minutes. As shown, the left-leg to right-leg pulse volume ratio, which is approximately one at the time of insertion, decreases to roughly half after fifty minutes.

Figure 3G:
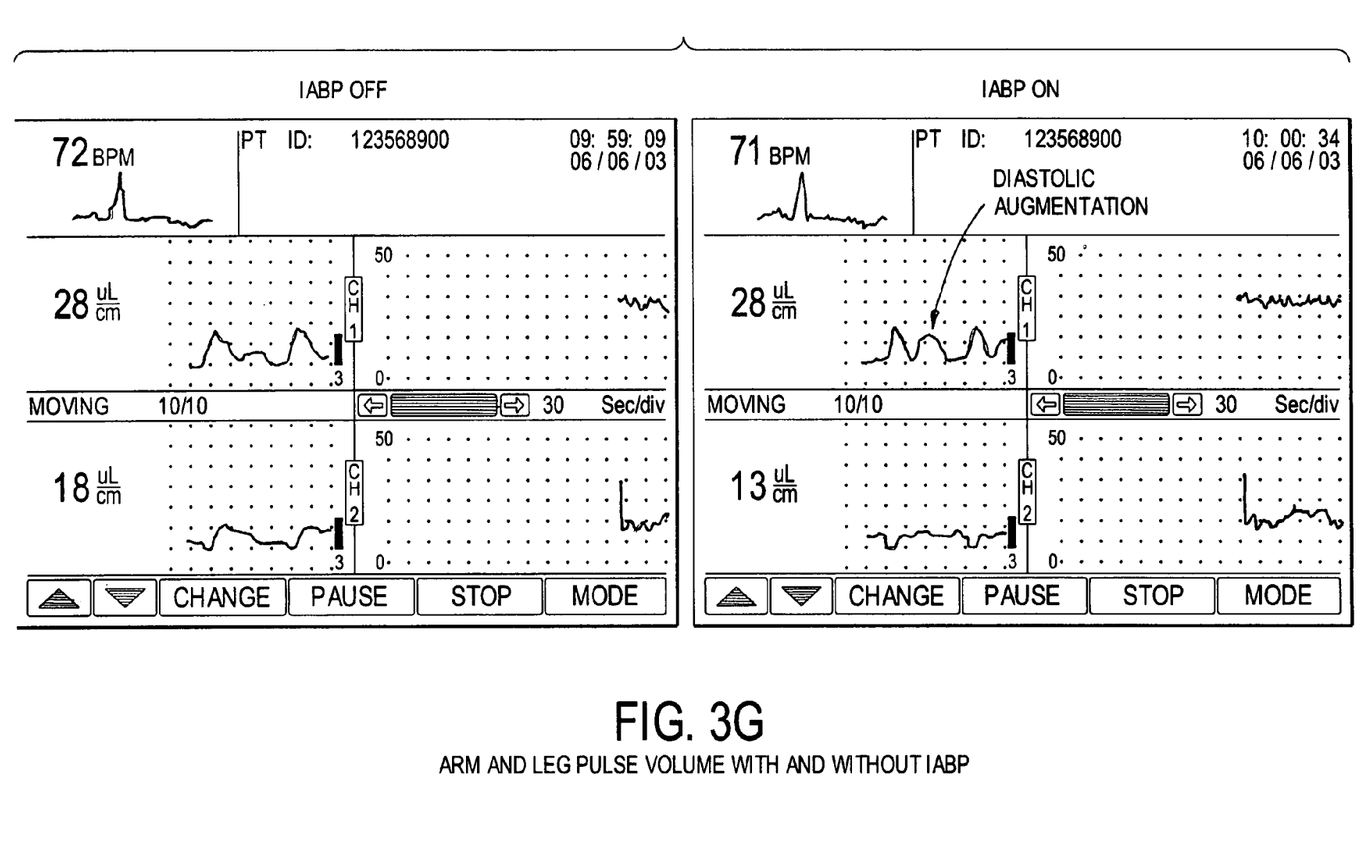
Figure 3H:
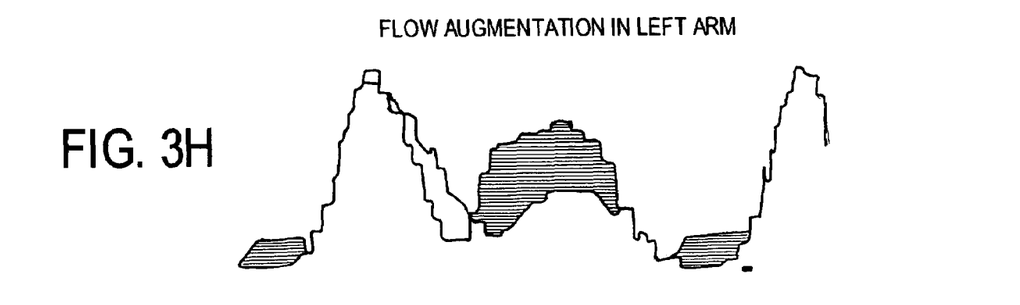
Figure 3I:
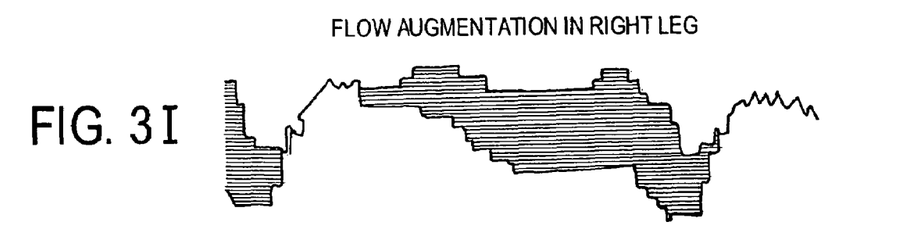

FIG. 3G shows arm and leg pulse volume with and without the intra-aortic balloon pump (pump off on the left, pump on on the right). FIGS. 3H and 3I show flow augmentation in the left arm and the right leg, respectively, as represented by the area between the curves representing flow with and without the pump.

8. Peripheral vascular disease: Currently there are no satisfactory quantitative methods for evaluating peripheral vascular disease. A standard device used in management of this problem is generally known as "pulse volume recordings" or PVR's. This technique uses multiple pneumatic plethysmographic cuffs which provide waveforms that indicate arterial pulsation but do not provide quantitative information about blood delivery to the tissues. The pulse volume device provides waveforms that coincide with peripheral vascular flow but, in addition, provides quantitative measurement of pulse volume and/or PNI (or PV-area or PV×HR). Pulse volume and/or PNI (or PV-area or PV×HR) measurements are made in these patients to evaluate the presence and degree of peripheral vascular disease. For example, the examination of one patient revealed that he had non-healing ulcers on his left leg. The PVR's were normal but pulse volume measurements in the left leg were only 15% of those measurements in the right leg. In addition, measurements are made before and after interventions to relieve peripheral vascular obstruction to see the effect of an intervention. Furthermore, where an intervention has been performed, the patient is followed periodically after intervention to detect recurrence of peripheral vascular obstruction.

9. Congestive heart failure: Congestive heart failure is associated with increased peripheral vascular resistance and decreased peripheral vascular flow. The pulse volume device is used in the detection of congestive heart failure. Ideally, pulse volume and/or PNI (or PV-area or PV×HR) measurements are made in ongestive heart failure patients when they are in good medical control. When a patient slips into heart failure, pulse volume and PNI (or PV-area or PV×HR) drop. In addition, the effectiveness of heart failure treatment is evaluated with pulse volume and/or PNI (or PV-area or PV×HR) measurements. When effective treatment is achieved, pulse volume and/or PNI (or PV-area or PV×HR) values return to normal.

10. Research evaluation of vasoactive medications: Currently, there are no satisfactory quantitative measurements in humans to evaluate the effectiveness of vasoactive medications. This makes clinical evaluation of these drugs problematic. The pulse volume device is used to quantitatively evaluate the effect of vasoactive medications. When a vasodilator is given to a patient, the pulse volume and/or PNI (or PV-area or PV×HR) increase. Relationships are developed between the dose of these medications and the degree of increase in the pulse volume and/or PNI (or PV-area or PV×HR) and these relationships are used to guide drug therapy.

11. Evaluation and treatment of syncope: Currently, patients who have fainting spells are frequently evaluated with "tilt testing." These tests involve bringing a patient from the horizontal to the vertical position. Patients who have vasovagal syncope often become symptomatic and faint when they are brought to the full upright position over a period of about half an hour. A positive tilt test is extremely discomforting to the patient and can produce cardiac arrhythmias. A decrease in pulse volume and/or PNI (or PV-area or PV×HR) is an early indicator of decreased peripheral vascular flow and therefore occurs well before a patient actually becomes symptomatic and faints. A brief, modified form of tilt test can be performed using the pulse volume device. A patient is allowed to lie recumbent for a period of about 10 minutes and then asked to stand. Those patients who are at risk for vasovagal syncope are expected to have an exaggerated decrease in pulse volume and/or PNI (or PV-area or PV×HR) when compared with normals. In addition, the effectiveness of treatment for syncope is evaluated with pulse volume and/or PNI (or PV-area or PV×HR). If effective treatment is being administered, the drop in pulse volume and/or PNI (or PV-area or PV×HR) experienced during an upright maneuver is diminished.

12. Detection and treatment of dehydration: When patients are dehydrated, there is a decrease in peripheral vascular flow and an increase in peripheral vascular resistance as the body tries to maintain the central circulating blood volume. When patients present with dehydration, their pulse volume and/or PNI (or PV-area or PV×HR) are diminished. Currently, the degree of dehydration is crudely estimated by clinical criteria, such as skin turgor, and intravenous fluids are administered on a formulated basis. The end point of dehydration is largely subjective and therefore a patient may spend too much or to little time receiving IV fluids and under medical observation than may be actually necessary. The return of pulse volume and/or PNI (or PV-area or PV×HR) to normal during fluid treatment of dehydration indicate that effective rehydration has occurred.

13. Pre-eclampsia: Pre-eclampsia is a condition in which there are acute changes in fluid content in the tissues. There is often edema which can be subjectively evaluated by the clinician. In addition to pulse volume measurement, the pulse volume device produces a signal which is proportional to total limb impedance. When a patient has an increase in electrolyte containing fluid due to progression of pre-eclampsia or eclampsia, total limb impedance decreases, and this can be detected by the pulse volume device.

14. Deep vein thrombosis: When venous return is compromised, the tissue in the limb swells. This causes a decrease in overall limb impedance which, as stated above, can be measured. If one limb has a much lower impedance than the contralateral limb, deep vein thrombosis is suspect.

15. Thermal injuries: Burns and frostbite are associated with decreased peripheral vascular flow to the affected area. The pulse volume device is used to evaluate the degree of thermal injury, and serial measurements are used to estimate the return of function as treatment progresses.

16. Renal Dialysis: Patients who are undergoing renal dialysis often experience vascular instability due to large fluid and electrolyte shifts. The pulse volume device is placed on the limb of patients undergoing renal dialysis. Large fluctuations in pulse volume and/or PNI (or PV-area or PV×HR) indicate that a patient may be at risk for developing vascular instability.

17. Radial Artery Harvesting: Radial arteries are now being used for coronary bypass grafts. It is important to make sure that the circulation to the hand is not compromised by radial artery resection. This requires that there is adequate magnitude and distribution of ulnar artery flow to the hand. The pulse volume device is used to make pulse volume and/or PNI (or PV-area or PV×HR). measurements from the fingers. Then, the radial artery is compressed. The measurements are repeated. Differences from the pre-compression measurements indicate those areas of the hand that are radial artery dependent.

18. Cardiac Output Monitoring: It is often desirable to monitor cardiac output, particularly during surgery or when managing critically ill patients. This requires the use of invasive techniques, such as thermal dilution or mixed venous oxygen measurement. The pulse volume device does not measure cardiac output. However, peripheral vascular flow is closely related to cardiac output. The pulse volume device is applied to patients in whom knowledge of cardiac output is considered desirable. Changes in pulse volume and/or PNI (or PV-area or PV×HR) occur with changes in cardiac output. This relationship has been observed both in the operating room and in animal testing.

19. Hypertension: Hypertension can have a number of different etiologies. In some cases the peripheral vasculature is reacting to excessive levels of native vasoconstrictors; in other cases the peripheral vasculature is abnormally non-compliant. Pulse volume analysis can help distinguish between these. When the peripheral vasculature is reactive, pulse volume may change when a vasodilator is given. When peripheral resistance is fixed, pulse volume does not change in response to vasodilators. Pulse volume and/or PNI (or PV-area or PV×HR) measurements may be useful in titrating anti-hypertensive drug doses.

20. Muscle Flow Capacity: Pulse volume in the calf increases after treadmill exercise. The degree of this increase is related to the ability of the muscle to adapt to exercise by providing increased flow. Pulse volume and/or PNI (or PV-area or PV×HR) measurements may therefore be useful as an index of athletic training. An individual may obtain baseline measurements prior to engaging in an exercise program. The changes in Pulse volume and/or PNI (or PV-area or PV×HR) measurements over time may provide a quantitative index of improving muscle exercise capacity.

Thus, the techniques disclosed above extend plethysmography to a wide variety Pulse volume and/or PNI (or PV-area or PV×HR). measurements of uses in which diagnoses have been traditionally carried out through more complicated or invasive techniques, or not at all.

While preferred embodiments of the present invention have been set forth in detail, those skilled in the art who have reviewed the disclosure will readily appreciate that other embodiments can be realized within the scope of the invention. For example, the present invention can be used in veterinary applications as well as with human patients. Therefore, the present invention should be construed as limited only by the appended claims.

We claim:

1. A method for detecting peripheral vascular disease in a patient, the method comprising:
   (a) taking quantitative pulse volume measurements at a plurality of positions on the patient's limbs through signal averaging; and
   (b) from the quantitative pulse volume measurements, detecting the peripheral vascular disease by calculating an area under a pulse volume curve for each of the patient's limbs.

2. The method of claim 1, wherein steps (a) and (b) are performed both before and after intervention to correct the peripheral vascular disease to determine whether the peripheral vascular disease has recurred.

3. The method of claim 1, wherein steps (a) and (b) are performed both before and after intervention to correct the peripheral vascular disease to determine an effectiveness of the intervention.

4. The method of claim 1, wherein step (b) comprises comparing the quantitative pulse volume measurements among the plurality of positions on the patent's limbs.

5. The method of claim 4, wherein the quantitative pulse measurement are compared for different limbs of the patient.

* * * * *